US008309126B2

(12) United States Patent
Holman et al.

(10) Patent No.: US 8,309,126 B2
(45) Date of Patent: *Nov. 13, 2012

(54) DISPERSIBLE BOSENTAN TABLET

(75) Inventors: Lovelace Holman, Arlesheim (CH); Timm Trenktrog, Binningen (DE)

(73) Assignee: Actelion Pharmaceuticals, Ltd., Allschwill (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/154,588

(22) Filed: Jun. 7, 2011

(65) Prior Publication Data

US 2011/0245281 A1   Oct. 6, 2011

Related U.S. Application Data

(63) Continuation of application No. 11/914,652, filed as application No. PCT/IB2006/051519 on May 15, 2006, now Pat. No. 7,959,945.

(30) Foreign Application Priority Data

May 17, 2005   (WO) ................. PCT/EP2005/005367

(51) Int. Cl.
A61K 9/20      (2006.01)
A61K 9/22      (2006.01)
A61K 31/506    (2006.01)
A01N 43/54     (2006.01)
C07D 403/00    (2006.01)
A61P 9/12      (2006.01)

(52) U.S. Cl. ........................ 424/465; 514/269; 544/296

(58) Field of Classification Search .................. 424/465; 514/269; 544/296
See application file for complete search history.

(56) References Cited

U.S. PATENT DOCUMENTS

| 5,747,068 | A  | * | 5/1998  | Mendizabal .............. 424/465 |
| 7,959,945 | B2 | * | 6/2011  | Holman et al. ........... 424/465 |
| 2003/0087911 | A1 | * | 5/2003  | Adams et al. .......... 514/252.17 |
| 2003/0232845 | A1 | * | 12/2003 | Dahanukar et al. ...... 514/263.36 |

FOREIGN PATENT DOCUMENTS

| WO | WO 2005/032553 | 4/2005 |
| WO | WO 2006/123285 | 11/2006 |

OTHER PUBLICATIONS

Data sheet "Tracleer® [bosentan] 62.5 mg and 125 mg film-coated tablets," FDA MEDWATCH, [online], Oct. 6, 2003, pp. 1-21.*
Package Leaflet for Tracleer (Package Leaflet: Information for the User, Actelion Pharmaceuticals, pp. 73-95, Jan. 2010).*
The European Public Assessment Report (EPAR) for Tracleer bosentan (European Medicines Agency, 2009, pp. 1-3).*
"Tracleer [bosentan] 62.5 mg and 125 mg film-coated tablets," FDA MEDWATCH, [online], (2003), pp. 1-21.
Kibbe, A.H., et al., *Handbook of Pharmaceutical Excipients*, 3rd Ed., American Pharmaceutical Association, Washington, USA and Pharmaceutical Press, London, (2000).
Lachman, L. et al., "The Theory and Practice of Industrial Pharmacy," 3rd Ed., pp. 883-902 (1986).

(Continued)

*Primary Examiner* — Aradhana Sasan
(74) *Attorney, Agent, or Firm* — Hoxie & Associates LLC

(57) ABSTRACT

The invention relates to dispersible tablets comprising the compound 4-tert-butyl-N-[6-(2-hydroxy-ethoxy)-5-(2-methoxy-phenoxy)-2-(pyrimidin-2-yl)-pyrimidin-4-yl]-benzenesulfonamide.

11 Claims, 1 Drawing Sheet

OTHER PUBLICATIONS

Office Action in Korean Patent Application No. 2007-7028463, Actelion Pharmaceuticals Ltd. (Aug. 28, 2009).
Remington's Pharmaceutical Sciences, 13$^{th}$ Ed., Mack Publishing Company, pp. 1907-1957 (1975).

Rosenzweig, et al., "Reply," Journal of the American College of Cardiology, Elsevier, NY, vol. 47, No. 9, pp. 1914-1915, (2006).

* cited by examiner

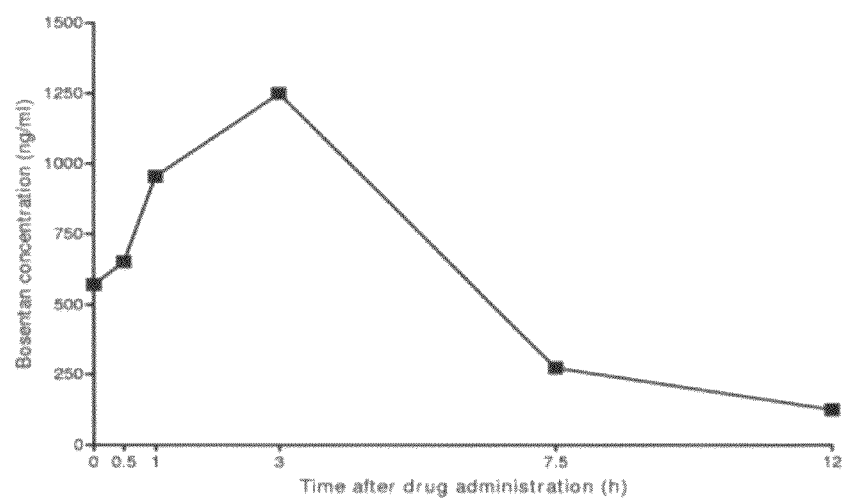

DISPERSIBLE BOSENTAN TABLET

This application is a continuation of U.S. patent application Ser. No. 11/914,652, filed Nov. 16, 2007, now U.S. Pat. No. 7,959,945, which is the national phase of International Application PCT/IB2006/051519 filed May 15, 2006, which in turn claims priority from International Application PCT/EP2005/005367, filed May 17, 2005, the contents of each of which are incorporated herein by reference.

The present invention relates to dispersible tablets comprising the compound 4-tert-butyl-N-[6-(2-hydroxy-ethoxy)-5-(2-methoxy-phenoxy)-2-(pyrimidin-2-yl)-pyrimidin-4-yl]-benzenesulfonamide, said compound being hereinafter referred to as compound I.

Compound I has the following formula:

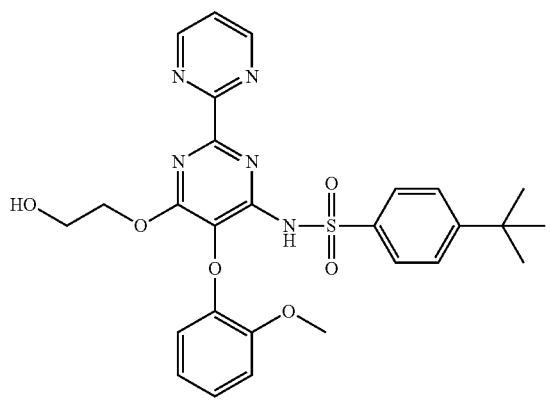

Compound I is an endothelin receptor inhibitor and useful for the treatment of pulmonary arterial hypertension (PAH). Compound I and the preparation thereof is disclosed in EP to 0526708 A1.

BRIEF DESCRIPTION OF THE DRAWING

FIG. 1 illustrates absorption based on PK data.

Bosentan (Tracleer®) is an oral treatment for PAH (Class III and IV in the United States, Class III in Europe). Bosentan is a dual endothelin receptor antagonist with affinity for both endothelin ETA and ETB receptors thereby preventing the deleterious effects of ET-1. As known from the World Standard Drug Database, the commercial available formulation has the following composition: bosentan (125 or 62.5 mg), starch, triacetin, magnesium stearate, talc, ferric oxide, povidone, titanium dioxide, ethylcellulose, glyceryl behenate, hypromellose and sodium starch glycollate.

Within the context of this disclosure, any reference to compound I is to be understood as referring also to pharmaceutically acceptable salts or solvates, including hydrates, of Compound I, as well as morphological forms thereof, if not indicated otherwise and where appropriate and expedient.

By "dispersible tablet" is meant a tablet, which disintegrates completely in water at 15-22° C. in not more than 5 minutes or preferably less than 4 minutes. In a further embodiment the dispersible tablets of the present invention have a disintegration time of less than 3 minutes, preferably less than 2 minutes or most preferred less than 1 minute (disintegration method according to the European Pharmacopoeia, EP).

The present drug product of compound I is currently being marketed as a tablet for the treatment of PAH, a deadly disease if untreated. Children have difficulties in taking tablets, thus the currently marketed tablet formulation is not convenient for administration to children. A drug product in the form of a suspension will be more children-friendly. The present invention therefore relates to the development of a tablet, which can be dispersed in water to form a suspension before administration. The dispersible tablet should disintegrate completely in water at 15-22° C. in less than 5 minutes or preferably less than 4 minutes. In a further embodiment the dispersible tablets of the present invention have a disintegration time of less than 3 minutes, preferably less than 2 minutes or most preferred less than 1 minute based on the method according to the European Pharmacopoeia (disintegration method according to the EP).

Further advantages of the paediatric formulation are the following:
- Better compliance due to special paediatric formulation
- It is now possible to give paediatric patients an optimized and individualized dosing according to body weight
- The paediatric formulation has demonstrated absorption based on pk data The present invention provides such a dispersible tablet suitable for children comprising: (a) compound I and (b) pharmaceutically acceptable excipients suitable for the preparation of dispersible tablets. The amount of compound I, calculated as the percentage of the content in weight of the active moiety, based on the total weight of the dispersible tablet, is 5% to 40%, preferably between 8% to 30%. In particular, the amount of compound I as active ingredient may vary from 10% to 17%.

In a preferred embodiment of the invention, the present invention provides a dispersible tablet wherein compound I is in the monohydrate form.

One or more pharmaceutically acceptable excipients may be present in the dispersible tablet, e.g. fillers (1.1), disintegrants (1.2), glidants (1.3), acidifying agents (1.4), flavouring agents (1.5), sweetening agents (1.6), and lubricants (1.7).

Reference is made to the extensive literature on the subject for these and other pharmaceutically acceptable excipients and procedures mentioned herein, see in particular Handbook of Pharmaceutical Excipients, Third Edition, edited by Arthur H. Kibbe, American Pharmaceutical Association, Washington, USA and Pharmaceutical Press, London; and Lexikon der Hilfsstoffe für Pharmazie, Kosmetik and angrenzende Gebiete edited by H. P. Fiedler, 4th Edition, Edito Cantor, Aulendorf and earlier editions.

Fillers (1.1) according to the invention include but are not restricted to microcrystalline cellulose, dicalcium phosphate, lactose and pregelatinized starch. Preferably, microcrystalline cellulose is used in combination with dicalcium phosphate.

Suitable disintegrants (1.2) according to the invention include but are not restricted to croscarmellose sodium, sodium starch glycolate, maize starch, CMC-Ca, CMC-Na, microcrystalline cellulose, cross-linked PVP, e.g. as known and commercially available under the trade names Crospovidone, Polyplasdone, available commercially from the TSP company, or Kollidon® XL, alginic acid, sodium alginate, pregelatinized starch, and guar gum. Preferably, Croscarmellose sodium, e.g. Ac-Di-Sol® is used.

As glidants (1.3), one or more of the following may be used: silica; colloidal silica, e.g. colloidal silica anhydrous, e.g. Aerosil® 200, magnesium trisilicate, powdered cellulose, starch and talc. Preferably, colloidal silicone dioxide is used.

Acidifying agents (1.4) include but are not restricted to tartaric acid, citric acid, ascorbic acid, lactic acid, and fumaric acid. Preferably tartaric acid is used Flavouring agents (1.5) include but are not restricted to Tutti Frutti, Strawberry, Banana, and Vanilla. Preferably Tutti Frutti is used.

Appropriate sweetening agents (1.6) according to the invention include but are not restricted to: Aspartame, acesulfame potassium, saccharin, saccharin sodium, sodium cyclamate, sucralose. Preferably the sweetening agents used are aspartame and acesulfame potassium.

Added flavouring agents as mentioned above and/or sweetening agents as mentioned above have the advantage to increase the compliance.

As lubricants (1.7) one or more of the following may be used Mg-, Al- or Ca-stearate, stearic acid, sodium stearyl fumarate, talc, sodium benzoate, glyceryl mono fatty acid, e.g. having a molecular weight of from 200 to 800 Daltons, e.g. glyceryl monostearate (e.g. Danisco, UK), glyceryl dibehenate (e.g. CompritolAT0888™, Gattefossé France), glyceryl palmito-stearic ester (e.g. Precirol™, Gattefossé France), polyethylene glycol (PEG, BASF), hydrogenated cotton seed oil (Lubitab, Edward Mendell Co Inc.), castor seed oil (Cutina H R, Henkel) and sucrose esters (Surfhope S E, Mitsubishi-Kagaku Foods Co.). Preferably, magnesium stearate, alone or in combination with glyceryl dibehenate, is used.

It will be appreciated that any given excipient may serve more than one function e.g. as filler, disintegrant, binder, glidant, and/or lubricant.

In a preferred embodiment, the dispersible tablet comprises the following pharmaceutically acceptable excipients: a) at least one filler (1.1) and b) at least one lubricant (1.7).

In another preferred embodiment, the dispersible tablet comprises the following pharmaceutically acceptable excipients: a) at least one filler (1.1), b) at least one lubricant (1.7) and c) at least one disintegrant (1.2).

It was found that the presence of an acidifying agent (1.4) decreases the solubility of compound I thus preventing tasting of the bitter taste of compound I when the tablet is dispersed with water e.g. on a spoon before administration. The bitter taste of compound I can also be overcome by using flavouring agents (1.5) and/or sweetening agents (1.6).

In one embodiment of the invention, the dispersible therefore comprises the following pharmaceutically acceptable excipients: at least one acidifying agent (1.4) and/or at least one flavouring agent (1.5) and/or at least one sweetening agent (1.6), preferably together with at least one filler (1.1) and at least one lubricant (1.7), preferably additionally comprising at least one disintegrant (1.2) and optionally also comprising at least one glidant (1.3).

According to the present invention, the amount of filler (1.1) may vary within a range of 40 to 85%, in particular 63 to 78% in weight based on the total weight of the dispersible tablet.

The amount of disintegrant (1.2) may vary within a range of from 0.5 to 20%, e.g. 1 to 15% in weight based on the total weight of the dispersible tablet.

The amount of glidant (1.3) may vary within ranges of from 0.1 to 5%, in particular 0.1 to 2.5%, especially 0.5 to 1.0% in weight based on the total weight of the dispersible tablet.

The amount of acidifying agent (1.4) may vary within ranges of from 0.5 to 13%, in particular 1 to 8% in weight based on the total weight of the dispersible tablet.

The amount of flavouring agent (1.5) may vary from 1 to 15%, preferably from 2 to 10% in weight based on the total weight of the dispersible tablet.

The amount of sweetening agent (1.6) may vary from 0.1 to 10%, preferably from 0.2 to 8%.

The amount of lubricant (1.7) may vary from 0.05 to 7%, preferably from 0.1 to 3.0%.

In a preferred aspect of the invention, the dispersible tablet comprises the following pharmaceutically acceptable excipients: one or more fillers (1.1), especially in a total amount of 40 to 85%, preferably from 63% to 78%, in weight based on the total weight of the dispersible tablet, one or more disintegrants (1.2), especially in a total amount of 0.5 to 20%, preferably from 1% to 15%, in weight based on the total weight of the dispersible tablet, one or more glidants (1.3), especially in a total amount of 0.1 to 5%, preferably from 0.5% to 1.0%, in weight based on the total weight of the dispersible tablet, one or more acidifying agents (1.4), especially in a total amount of 0.5 to 13%, preferably from 1% to 8%, in weight based on the total weight of the dispersible tablet, one or more flavouring agents (1.5), especially in a total amount of 1 to 15%, preferably from 2% to 10%, in weight based on the total weight of the dispersible tablet, one or more sweetening agents (1.6), especially in a total amount of 0.1 to 10%, preferably from 0.2 to 8%, in weight based on the total weight of the dispersible tablet, and one or more lubricants (1.7), especially in a total amount of 0.05 to 7%, preferably from 0.1% to 3.0%, in weight based on the total weight of the dispersible tablet.

The absolute amounts of each pharmaceutically acceptable excipient and the amounts relative to other pharmaceutically acceptable excipients is dependent on the desired properties of the dispersible tablet and may be chosen by routine experimentation.

The tablets of the invention are dispersible, e.g. in aqueous media such as water. The tablets can thus be dispersed in e.g. water before administration, which is a convenient form of administration for children. This also leads to a better patient compliance. The dispersible tablets of the present invention have a disintegration time of less than 5 minutes or preferably less than 4 minutes. In a further embodiment the dispersible tablets of the present invention have a disintegration time of less than 3 minutes, preferably less than 2 minutes or most preferred less than 1 minute based on the method according to the European Pharmacopoeia.

According to the invention, the process for the preparation of the dispersible tablets comprises mixing the excipients of phase II (about 10-20 minutes), adding it to phase I and re-mixing for the same period of time. Phase III is then added to the powder mixture of phases I and II and mixed for about 2-5 minutes and compressed into tablets.

Phase I comprises compound I and one or more pharmaceutically acceptable excipients which are present in a concentration of more than 5% in weight based on the total weight of the dispersible tablet.

Phase II comprises the pharmaceutically acceptable excipients which are present in a concentration of less than 5% in weight based on the total weight of the dispersible tablet with the exception of the lubricants of the stearate type.

Phase III comprises lubricants of the stearate type.

Procedures which may be used may be conventional or known in the art or based on such procedures e.g. those described in L. Lachman et al., The Theory and Practice of Industrial Pharmacy, 3rd Ed., 1986; H. Sucker et al., Pharmazeutische Technologie, Thieme, 1991; Hagers Handbuch der pharmazeutischen Praxis, 4th Ed. (Springer Verlag, 1971) and Remington's Pharmaceutical Sciences, 13th Ed., (Mack Publ., Co., 1970) or later editions.

Since compound I is practically insoluble in water, it was a surprise that despite the general knowledge that direct compression (i.e. compression without previous wet granulation) does not enhance the dissolution of compounds with low solubility, compound I exhibits good dissolution from the dispersible tablets of the present invention obtained by the method of direct compression.

In fact, the dissolution of compound I from the dispersible tablets of the invention is such that more than 60%, especially more than 70% w/w of compound. I is dissolved within 15 minutes when tested in 900 ml of phosphate buffer (pH=6.8) with 0.1% w/v sodium lauryl sulphate heated to 37° C. and stirred at 100 rpm with a paddle as described in the United States Pharmacopoeia.

In one aspect of the invention one or more lubricants may be sprayed on the material contacting surfaces of pressing tools, e.g. punches and/or dies, of the tabletting machine before compression.

The physical and chemical stability of the dispersible tablets may be tested in conventional manner, e.g. by measurement of dissolution, friability, disintegration time, assay for compound I degradation products, appearance and/or microscopy, e.g. after storage at room temperature, i.e. 25° C./60% r.h. (relative humidity), and/or storage at 40° C./75% r.h.

The dissolution rate is stable over time and different storage conditions. In a preferred embodiment the dissolution rate of the tablets is stable over at least 6 months when they are stored at 25° C./60% r.h. and 40° C./75% r.h.

The dispersible tablets may vary in shape and be, for example, round, oval, oblong, cylindrical, clover-shaped or any other suitable shape.

In a preferred embodiment of the invention dispersible tablets obtained by the compression method described above are clover shaped or round. The edges of the dispersible tablets may be beveled or rounded. Most preferably, the dispersible tablets are clover shaped with beveled edges. The dispersible tablets according to the invention may be scored or engraved.

The dispersible tablet according to the invention is preferably clover-shaped, quadrisected with beveled edges. The dispersible tablet has a diameter ranging between 8 and 15 mm, most preferably between 9 and 11 mm. Its thickness is ranging from 2.5 to 4.5 mm, preferably between 2.9 and 3.9 mm.

The dispersible tablets of the invention comprising about 32 mg of compound I as active moiety may have a hardness of from about 50 to 120 N, preferably 60 to 100 N.

The dispersible tablets of the invention may be colored and/or marked so as to impart an individual appearance and to make them instantly recognizable. The use of dyes can serve to enhance the appearance as well as to identify the dispersible tablets. Dyes suitable for use in pharmacy typically include carotinoids, iron oxides or chlorophyll. The dispersible tablets of the invention may be marked using an imprint code.

The dispersible tablets of the present invention are useful for the treatment of PAH and exhibit a good pharmacokinetic profile. The dispersible tablets of the present invention can be administered e.g. twice daily with an effective dosing of the active ingredient compound I in the range of 2 mg/kg to 4 mg/kg body weight.

The tablet may be packed in any possible blister known in the art, as for example into aluminum blisters.

As can be seen from FIG. 1, the paediatric formulation has demonstrated absorption based on pk data.

The following non-limitative examples illustrate the invention.

EXAMPLE 1

|  | Components | Amount per Tablet [mg] | Percent [w/w] |
|---|---|---|---|
| Phase I | Compound I as monohydrate, micronized | 33.045 | 11.39 |
|  | Microcrystalline cellulose (1.1) | 116.265 | 40.09 |
|  | Dicalcium phosphate (1.1) | 101.500 | 35.00 |
| Phase II | Croscarmellose sodium (1.2) | 11.600 | 4.00 |
|  | Colloidal silicone dioxide (1.3) | 2.900 | 1.00 |
|  | Tartaric acid (1.4) | 7.000 | 2.41 |
|  | Tutti Frutti (1.5) | 9.000 | 3.10 |
|  | Aspartame (1.6) | 3.700 | 1.28 |
|  | Acesulfame potassium (1.6) | 1.800 | 0.62 |
| Phase III | Magnesium stearate (1.7) | 3.190 | 1.1 |
|  | Total | 290 |  |

Tablet Properties:

| Parameter | Value |
|---|---|
| Diameter | 10 mm |
| Friability | <0.3% |
| Disintegration at 15-22° C. (EP) | <40 secs |
| Dissolution, mean of 6 tablets Paddle method, 100 rpm, phosphate buffer at pH = 6.8 with 0.1% sodium lauryl sulphate, 37° C. | More than 75% within 15 minutes |

EXAMPLE 2

|  | Components | Amount per Tablet [mg] | Percent [w/w] |
|---|---|---|---|
| Phase I | Compound I as monohydrate | 33.045 | 11.80 |
|  | Microcrystalline cellulose (1.1) | 135.200 | 48.29 |
|  | Dicalcium phosphate (1.1) | 70.000 | 25.00 |
| Phase II | Croscarmellose sodium (1.2) | 11.200 | 4.00 |
|  | Colloidal silicone dioxide (1.3) | 2.800 | 1.00 |
|  | Tartaric acid (1.4) | 6.250 | 2.23 |
|  | Tutti Frutti (1.5) | 9.000 | 3.21 |
|  | Aspartame (1.6) | 3.700 | 1.32 |
|  | Acesulfame potassium (1.6) | 1.800 | 0.64 |
|  | Glyceryl dibehenate (1.7) | 5.600 | 2.00 |
| Phase III | Magnesium stearate (1.7) | 1.400 | 0.50 |
|  | Total | 280 |  |

Tablet Properties:

| Parameter | Value |
|---|---|
| Diameter | 10 mm |
| Friability | <0.3% |
| Disintegration at 15-22° C. (EP) | <40 secs |
| Dissolution, mean of 6 tablets Paddle method, 100 rpm, phosphate buffer at pH = 6.8 with 0.1% sodium lauryl sulphate, 37° C. | More than 75% within 15 minutes |

EXAMPLE 3

|  | Components | Amount per Tablet [mg] | Percent [w/w] |
|---|---|---|---|
| Phase I | Compound I as monohydrate | 33.045 | 15.74 |
|  | Microcrystalline cellulose (1.1) | 79.765 | 37.98 |
|  | Dicalcium phosphate (1.1) | 63.000 | 30.00 |
| Phase II | Croscarmellose sodium (1.2) | 8.400 | 4.00 |
|  | Colloidal silicone dioxide (1.3) | 2.100 | 1.00 |
|  | Tartaric acid (1.4) | 6.250 | 2.98 |
|  | Strawberry (1.5) | 9.000 | 4.29 |
|  | Aspartame (1.6) | 3.700 | 1.76 |
|  | Acesulfame potassium (1.6) | 1.800 | 0.86 |
| Phase III | Magnesium stearate (1.7) | 2.940 | 1.40 |
|  | Total | 210 |  |

Tablet Properties:

| Parameter | Value |
|---|---|
| Diameter | 9 mm |
| Friability | <0.3% |
| Disintegration at 15-22° C. (EP) | <40 secs |
| Dissolution, mean of 6 tablets Paddle method, 100 rpm, phosphate buffer at pH = 6.8 with 0.1% sodium lauryl sulphate, 37° C. | More than 75% within 15 minutes |

The invention claimed is:

1. A dispersible tablet composition comprising an active ingredient consisting of compound I of the formula

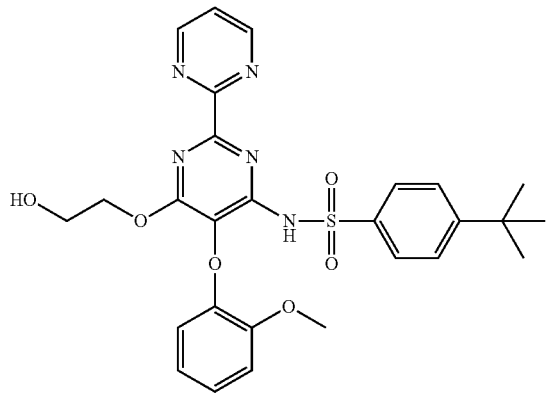

or a pharmaceutically acceptable salt or solvate thereof, and pharmaceutically acceptable excipients.

2. The dispersible tablet according to claim 1 comprising the following pharmaceutically acceptable excipients: a) at least one filler and b) at least one lubricant.

3. The dispersible tablet according to claim 2 further comprising at least one disintegrant.

4. The dispersible tablet according to any one of the preceding claims comprising at least one acidifying agent and/or at least one flavouring agent and/or at least one sweetening agent.

5. The dispersible tablet according to claim 1 comprising the following pharmaceutically acceptable excipients: one or more fillers in a total amount of 40 to 85% in weight based on the total weight of the dispersible tablet, one or more disintegrants in a total amount of 0.5 to 20% in weight based on the total weight of the dispersible tablet, one or more glidants in a total amount of 0.1 to 5% in weight based on the total weight of the dispersible tablet, one or more acidifying agents in a total amount of 0.5 to 13% in weight based on the total weight of the dispersible tablet, one or more flavouring agents in a total amount of 1 to 15% in weight based on the total weight of the dispersible tablet, one or more sweetening agents in a total amount of 0.1 to 10% in weight based on the total weight of the dispersible tablet, and one or more lubricants in a total amount of 0.05 to 7% in weight based on the total weight of the dispersible tablet.

6. The dispersible tablet according to any one of the preceding claims wherein compound I is in the monohydrate form.

7. The dispersible tablet according to any one of the preceding claims obtainable by using the method of direct compression.

8. A method for treating pulmonary arterial hypertension, comprising dispersing the dispersible tablet of claim 1 in aqueous media to form a suspension and administering the suspension to a patient in need thereof.

9. A process for the preparation of a dispersible tablet according to any one of claims 1 to 7, characterized in that the tablet is prepared by direct compression.

10. The dispersible tablet of claim 1, wherein the pharmaceutically acceptable excipients include a flavoring agent and/or a sweetener.

11. The dispersible tablet of claim 1 which disintegrates completely in water at 15-22° C. in not more than 5 minutes.

* * * * *